US008437866B2

(12) United States Patent  (10) Patent No.: US 8,437,866 B2
Gebauer et al.  (45) Date of Patent: May 7, 2013

(54) INTERNALLY INTERCONNECTED ELECTRODE ASSEMBLY FOR A LEAD AND METHOD THEREFOR

(75) Inventors: Aaron Gebauer, St. Paul, MN (US); Devon N. Arnholt, Minneapolis, MN (US); Gregory L. Sundberg, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1495 days.

(21) Appl. No.: 11/127,933

(22) Filed: May 12, 2005

(65) Prior Publication Data

US 2006/0259105 A1 Nov. 16, 2006

(51) Int. Cl.
A61N 1/22 (2006.01)
(52) U.S. Cl.
USPC .............................. 607/122; 607/37
(58) Field of Classification Search .................. 607/137, 607/115–122, 37–38
See application file for complete search history.

(56) References Cited

U.S. PATENT DOCUMENTS

| 3,657,744 | A |   | 4/1972  | Ersek |
| 5,056,517 | A | * | 10/1991 | Fenici ................................ 607/2 |
| 5,304,219 | A |   | 4/1994  | Chernoff et al. |
| 5,385,409 | A |   | 1/1995  | Ide |
| 5,487,757 | A |   | 1/1996  | Truckai et al. |
| 5,669,790 | A |   | 9/1997  | Carson et al. |
| 6,026,567 | A |   | 2/2000  | Swoyer et al. |
| 6,434,430 | B2 |   | 8/2002  | Borgersen et al. |
| 6,623,480 | B1 |   | 9/2003  | Kuo et al. |
| 6,650,921 | B2 | * | 11/2003 | Spehr et al. .................... 600/374 |
| 6,725,096 | B2 |   | 4/2004  | Chinn et al. |
| 6,785,576 | B2 |   | 8/2004  | Verness |
| 6,792,317 | B1 |   | 9/2004  | Doan et al. |
| 6,912,423 | B2 |   | 6/2005  | Ley et al. |
| 7,160,311 | B2 |   | 1/2007  | Barrus et al. |
| 7,175,478 | B2 |   | 2/2007  | Ollivier |
| 7,234,977 | B2 |   | 6/2007  | Westlund et al. |
| 7,648,401 | B2 |   | 1/2010  | Guenther et al. |
| 7,962,213 | B2 |   | 6/2011  | Arnholt et al. |
| 8,126,557 | B2 |   | 2/2012  | Jang et al. |
| 2001/0037135 | A1 | * | 11/2001 | Pianca et al. ................... 607/122 |
| 2002/0029074 | A1 | * | 3/2002  | Treaba et al. .................. 607/137 |
| 2002/0077685 | A1 | * | 6/2002  | Sundquist et al. ............ 607/116 |
| 2003/0023294 | A1 | * | 1/2003  | Krall et al. ..................... 607/122 |
| 2003/0036779 | A1 |   | 2/2003  | Westlund et al. |
| 2003/0074031 | A1 | * | 4/2003  | Ley et al. ......................... 607/37 |
| 2004/0054390 | A1 |   | 3/2004  | Zarembo et al. |
| 2004/0064174 | A1 | * | 4/2004  | Belden ........................... 607/122 |
| 2004/0068313 | A1 |   | 4/2004  | Jenney et al. |
| 2004/0215282 | A1 |   | 10/2004 | Weijden et al. |
| 2004/0215303 | A1 |   | 10/2004 | Sage |
| 2004/0230268 | A1 |   | 11/2004 | Huff et al. |
| 2005/0027325 | A1 |   | 2/2005  | Lahti et al. |
| 2006/0041299 | A1 | * | 2/2006  | Bauer et al. .................... 607/125 |
| 2007/0027517 | A1 |   | 2/2007  | Bischoff et al. |
| 2008/0027504 | A1 |   | 1/2008  | Bedenbaugh |
| 2008/0046059 | A1 |   | 2/2008  | Zarembo et al. |

(Continued)

OTHER PUBLICATIONS

International Search Report and Written Opinion issued in PCT/US2010/057025 dated Mar. 2, 2011.

*Primary Examiner* — Rex R Holmes
(74) *Attorney, Agent, or Firm* — Faegre Baker Daniels LLP

(57) ABSTRACT

An internally connected interconnect for an electrode and method for forming same.

11 Claims, 7 Drawing Sheets

U.S. PATENT DOCUMENTS

2008/0114230 A1 5/2008 Addis
2008/0154328 A1 6/2008 Thompson et al.
2011/0159748 A1 6/2011 Lim et al.
2011/0208282 A1 8/2011 Arnholt et al.

* cited by examiner

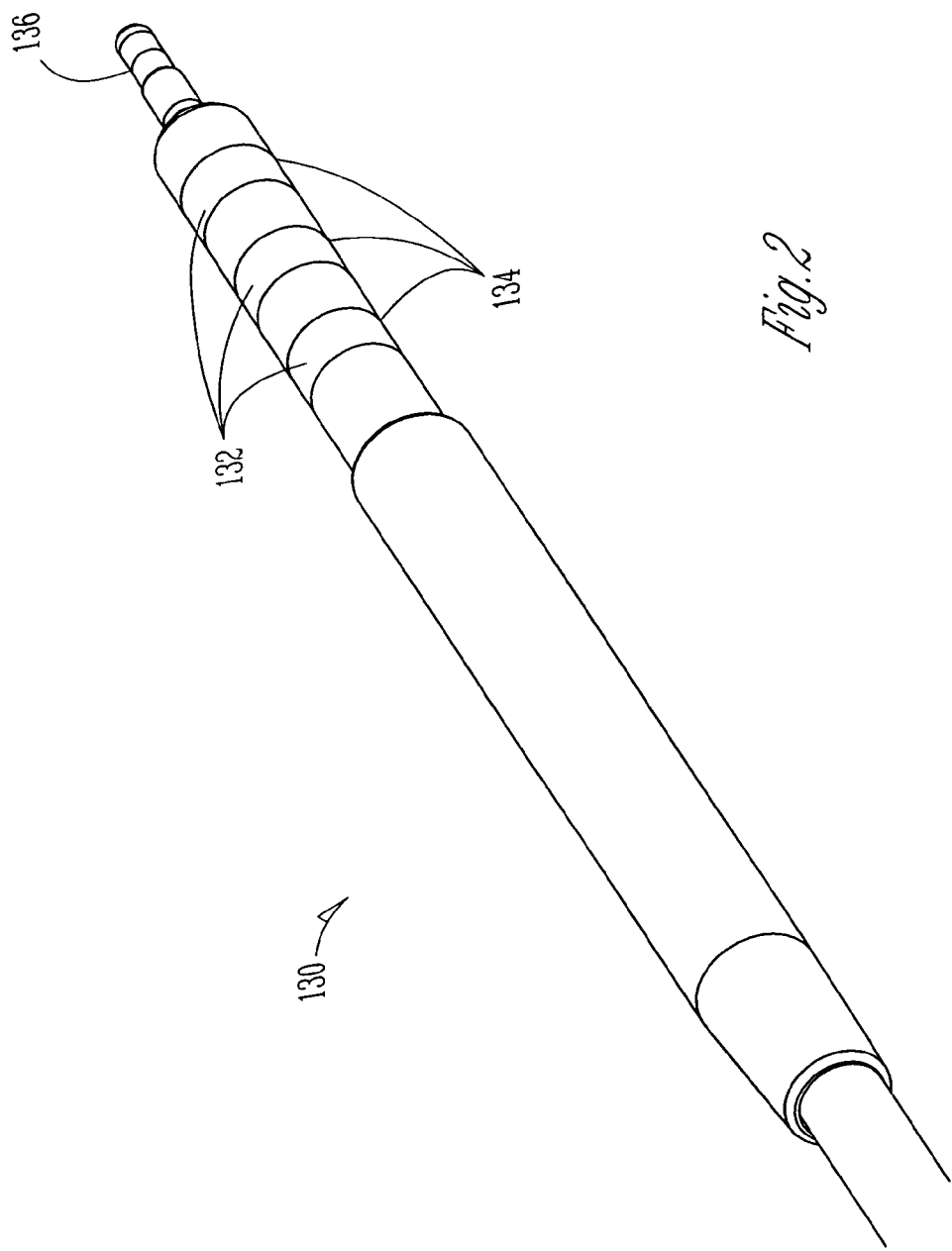

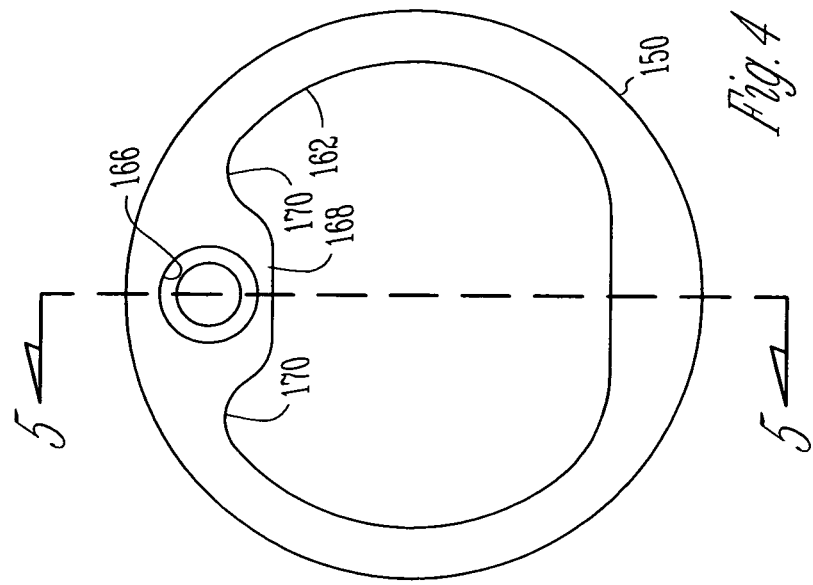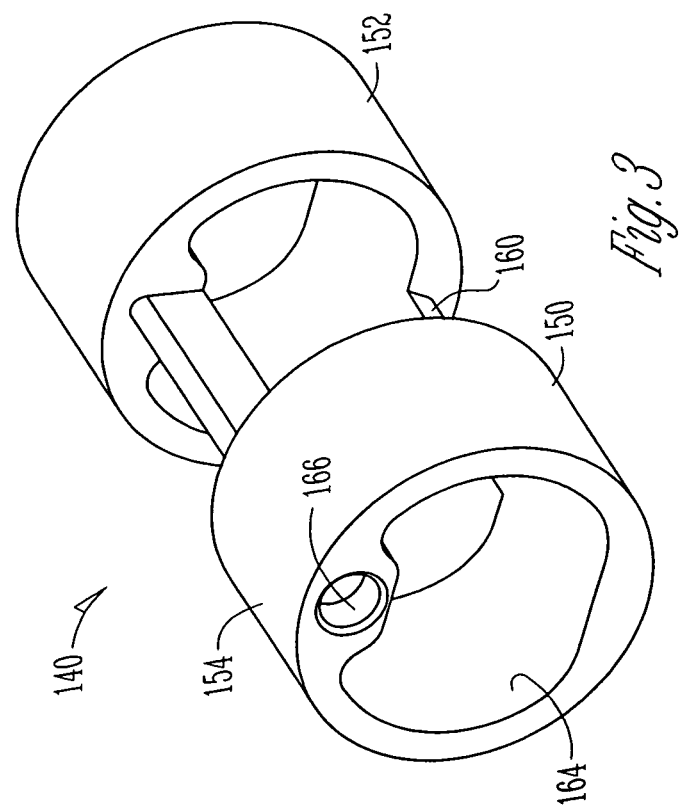

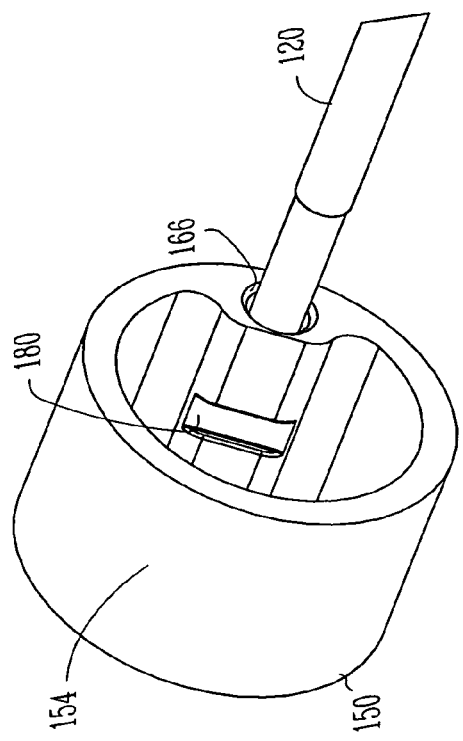
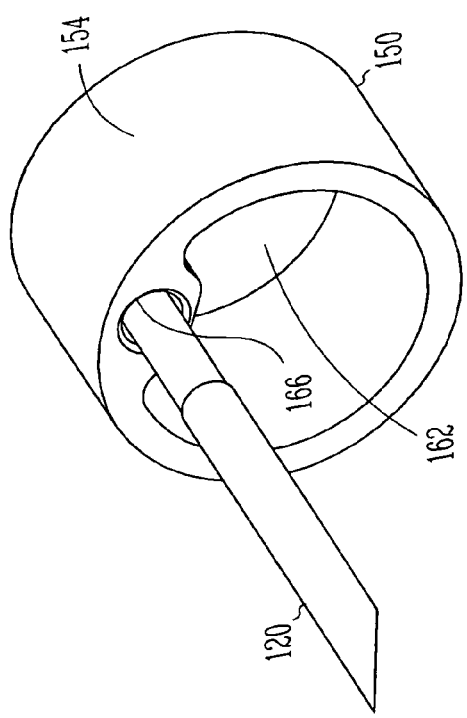

INTERNALLY INTERCONNECTED ELECTRODE ASSEMBLY FOR A LEAD AND METHOD THEREFOR

TECHNICAL FIELD

Connector assembly for leads which conduct electrical signals to and from the heart, and more particularly, an internally interconnected connector assembly for a lead.

TECHNICAL BACKGROUND

Pacemaker leads represent the electrical link between the pulse generator and the heart tissue, which is to be excited and/or sensed. These pacemaker leads include single or multiconductors that are connected to an electrode in an electrode assembly at an intermediate portion or distal end of a pacing lead. A connector is included at the proximal end to form the electrical connection with the pacemaker.

When leads with multiple conductors are involved, the conductors are individually, mechanically and electrically coupled with the pulse generator at a proximal end of the multiple conductors, and can be coupled at a distal end or an intermediate portion with tissue electrodes. The multiple conductors are electrically insulated from each other to prevent shorts and limit electrical leakage between conductors. While lead design favors compact size, mechanical joints should be strong and secure, and electrical contact surfaces should remain pristine and uniform. To accommodate these assembly criteria, conventional assemblies constitute multiple separate unipolar electrodes, or relatively bulky multipolar designs. Furthermore, conventional assemblies have manufacturing or performance drawbacks, for example, the assembly process is difficult and time consuming.

Accordingly, what is needed is an improved electrode joint design, and a related method to assemble the joint without disruption to outer electrode surfaces.

SUMMARY

A lead assembly includes an electrode defined in part by an outer contact surface, where the electrode further has a first major inner lumen, and a second inner lumen disposed between the first major lumen and the outer surface. Deformable material, such as a projection, is optionally disposed adjacent the second inner lumen. The assembly further includes at least one conductor disposed within the second inner lumen. The assembly optionally further includes a lead body with a tissue electrode therealong, and a conductor within the lead body.

Several options for the lead assembly are as follows. For example, the second inner lumen has a first uncollapsed position and a second collapsed position. The second inner lumen, optionally, has one or more recesses adjacent thereto.

A method is further provided including retaining an electrode of a terminal electrode, the electrode defined in part by an outer contact surface, the electrode having a first major inner lumen defined by a first inner surface, the electrode having at least an inner lumen disposed between the first major lumen and the outer surface. The method further includes disposing at least one conductor within the inner lumen, applying mechanical force to an inner surface of an electrode, for example without deforming the outer surface, and deforming material of the electrode adjacent to the at least one inner lumen.

Several options for the method are as follows. For example, in one option, the method further includes disposing at least a portion of deformed material into one or more recesses adjacent to the at least one inner lumen. In another option, the method includes at least partially collapsing the at least one lumen and mechanically coupling the at least one conductor with the electrode. The at least partial collapsing includes, in one option, moving a tool portion within a major lumen of the electrode, and moving the tool portion toward the inner lumen.

These and other embodiments, aspects, advantages, and features will be set forth in part in the description which follows, and in part will become apparent to those skilled in the art by reference to the following description and referenced drawings or by practice thereof. The aspects, advantages, and features are realized and attained by means of the instrumentalities, procedures, and combinations particularly pointed out in the appended claims and their equivalents.

BRIEF DESCRIPTION OF THE DRAWINGS

FIG. 2 is a perspective view of a portion of a lead constructed in accordance with at least one embodiment.

FIG. 3 is a perspective view of a terminal electrode device constructed in accordance with at least one embodiment.

FIG. 4 is an end view of a terminal electrode device constructed in accordance with at least one embodiment.

FIG. 6 is a perspective view of a terminal electrode device constructed in accordance with at least one embodiment.

FIG. 7 is a perspective view of a terminal electrode device constructed in accordance with at least one embodiment.

DESCRIPTION OF THE EMBODIMENTS

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
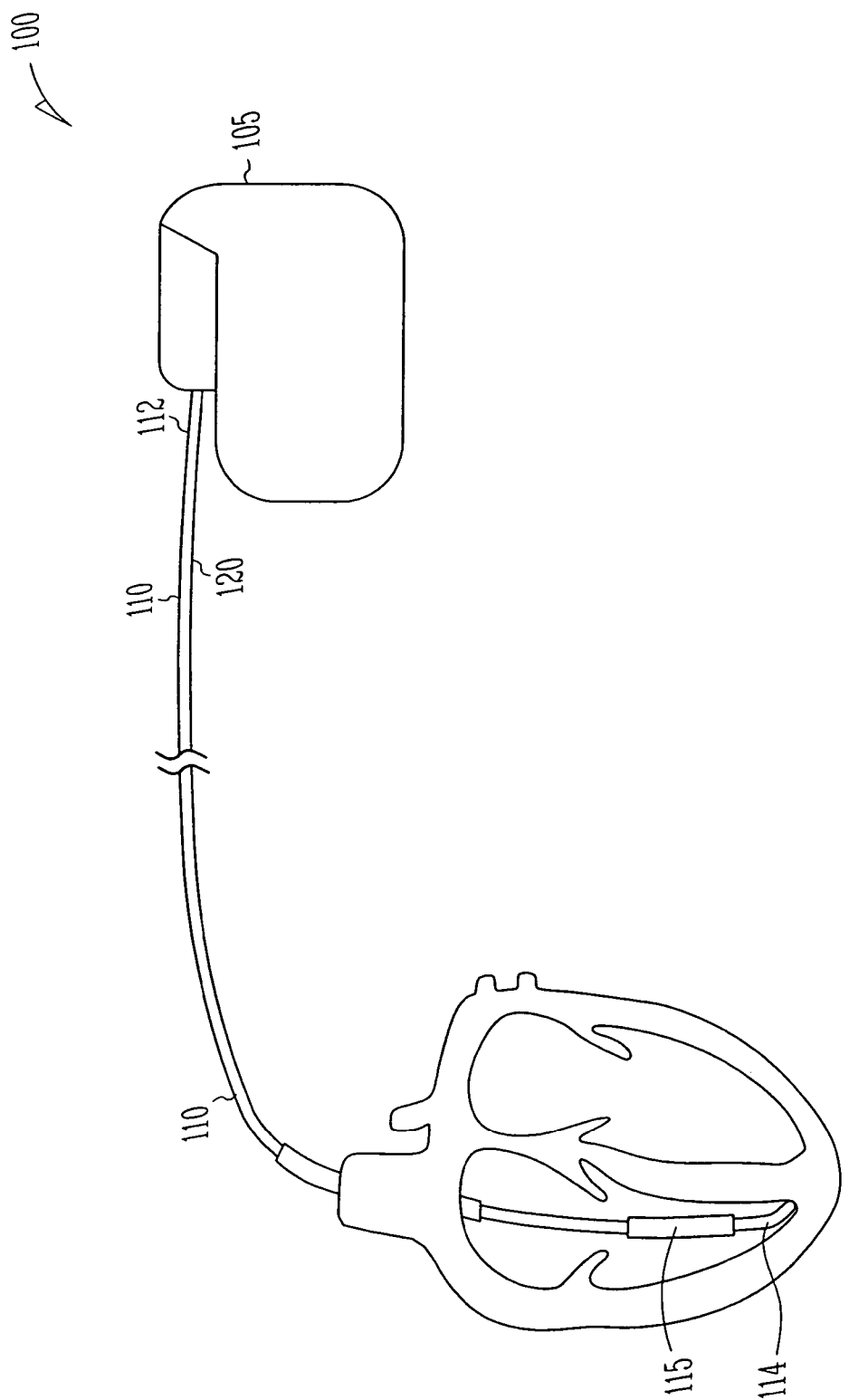
FIG. 1 is a diagram illustrating a lead system constructed in accordance with one embodiment.

An implantable device 100, such as a lead for use with an electrical stimulator 105, is illustrated in FIG. 1. The implantable device 100 includes a lead body 110, and at least one conductor 120 contained within the lead body 110. One example of a conductor includes, but is not limited to, an elongate conductor. The lead body 110 extends from a proximal end 112 to a distal end 114. The proximal end 112 of the lead is electrically coupled with the electrical stimulator 105, for example, with a connector assembly 130 (FIG. 2).

In one option, the electrical stimulator 105 is a pulse sensor and generator that contains electronics to sense various electrical signals of the heart and also produce current pulses for delivery to the heart. The pulse sensor and generator also contains electronics and software necessary to detect certain types of arrhythmias and to correct for them.

The implantable device 100 further includes, in one option, one or more electrodes 115. The one or more electrodes 115 are each electrically coupled with the at least one conductor 120. The electrode 115 allows for electrical signals to be delivered to the tissue of the heart, for example, from the electrical stimulator 105. The implantable device 100 further includes, in one option, features to allow the lead body to be fixated within a patient. For example, in one option, the lead body includes passive fixation features, such as one or more tines allowing the lead assembly to be fixation within or near a heart. In another option, the lead body includes an active fixation assembly, such as a fixation helix.

Referring to FIG. 2, a connector assembly 130 is illustrated in greater detail, where one example of a multipolar inline lead terminal is illustrated. The terminal connector assembly 130 is configured to physically mate with a pulse sensor and generator, and to electrically couple with the pulse sensor and generator. In one example, the connector assembly 130 includes one or more electrodes 132, such as, for example, three terminal rings 134. The connector assembly 130 further includes a terminal pin 136.

FIG. 3 illustrates several options for portions of the connector assembly, for example, a terminal electrode assembly 140. The terminal electrode assembly 140 is an elongate structure that includes at least a first electrode 150 and a second electrode 152, where the first electrode 150 and the second electrode 152 are defined in part by an outer contact surface 154. Disposed between the first electrode 150 and the second electrode 152 is at least one electrode interconnect 160, where the at least one electrode interconnect 160 electrically and/or mechanically interconnects the first and second electrodes 150, 152. It should be noted that the terminal electrode assembly 140 can include one or more electrodes, and is not limited to a two-electrode structure.

FIG. 4 illustrates an end view of an example of the first electrode 150. It should be noted that the features discussed herein for the first electrode 150 are described for a terminal electrode. However, the features discussed herein can also be incorporated with other types of structure, including, but not limited to tissue electrodes disposed along the lead or lead body.

The first electrode 150 includes a first major inner lumen 162, defined in part by a first inner surface 164 (FIG. 3). The first major inner lumen 162, in one option, has a cross-sectional shape as illustrated in FIG. 4. The shape of the inner lumen 162, in one option, is larger than the second inner lumen 166. The major inner lumen 162 shape can have a variety of cross-sections, for example, shapes which allow for the second inner lumen 166, and variations associated therewith.

The first electrode 150 further includes a second inner lumen 166, that optionally allows for a conductor (FIG. 1) to be inserted and coupled therein, where the second inner lumen 166 has, optionally, a substantially circular cross-section. The second inner lumen 166, for example, forms an inner conductor lumen. The second inner lumen 166 is disposed between the first major lumen 162 and the outer surface. It should be noted that additional lumens can be provided for the electrodes, for example, for additional conductors to be disposed therein. Furthermore, in another option, more than one conductor can be disposed within the lumen. In an option, the second inner lumen is defined by a surface, and the surface is a textured surface.

The second inner lumen 166 has a circular cross-section, in one example. It should be noted that other cross-sectional shapes are possible as well, including, but not limited to oval, elliptical, or cross-sections with one or more planar sides. Further options for the second inner lumen 166 include a lumen(s) that are blind or thru holes, and may include features for ease of assembly, such as a tapered entry perimeter.

Figure 5:
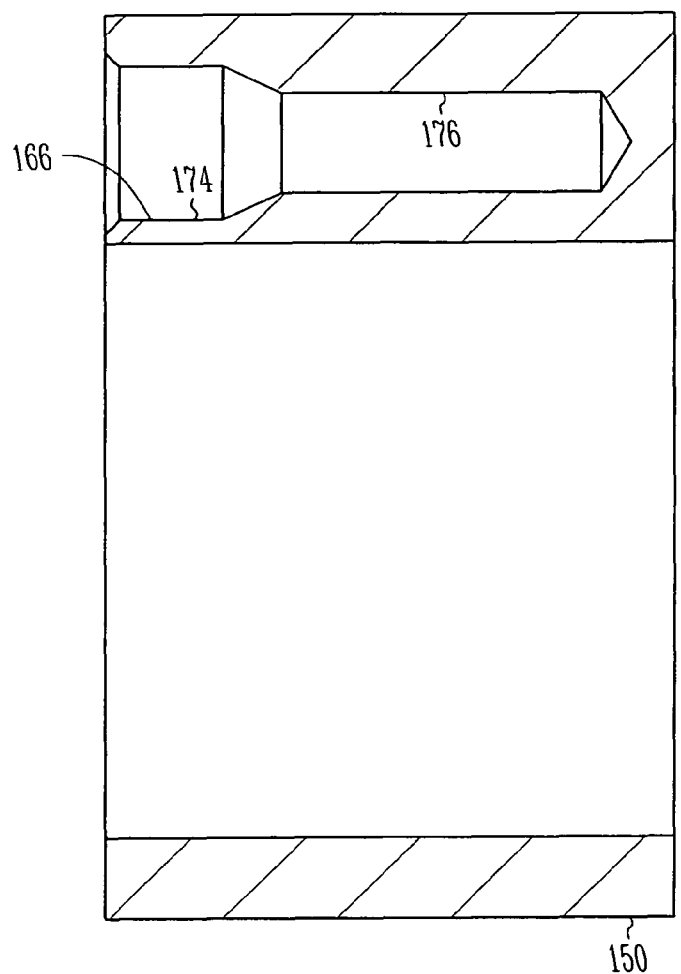
FIG. 5 is a cross-sectional view of a terminal electrode device taken along 5-5 of FIG. 4.

In one option, a deformable projection 168 is disposed adjacent to the second inner lumen 166, where at least a portion of the second inner lumen 166 and/or the deformable projection 168 has a first uncollapsed position, and a second collapsed position, as further described below. FIG. 5 illustrates a cross-section of the first electrode 150, illustrating options for the second inner lumen 166 in greater detail. For example, in one option, the second inner lumen 166 includes a first diameter 174 and a second diameter 176 where it is tapered therebetween. The first diameter 174 allows for the conductor to be threaded therein before the process to couple the conductor with the electrode 150.

Referring again to FIG. 4, the first electrode 150 further optionally includes one or more recesses 170 disposed adjacent to the second inner lumen 166 and/or the deformable projection 168. The one or more recesses 170 allow for material displacement from the deformable projection 168 when the deformable projection 168 and/or the inner lumen 166 are collapsed. In one option, at least two recesses on either side of the deformable projection 168 are present.

Referring to FIG. 6, a conductor 120 is disposed within the inner conductor lumen 166 of the electrode 150, where the inner conductor lumen 166 is adjacent to the major lumen 162. The conductor 120 provides the electrical connection between the electrode 150 and the tissue electrode (FIG. 1), where the electrode 150 is electrically coupled with the energy source (FIG. 1).

FIG. 7 illustrates the conductor 120 disposed within the inner conductor lumen 166, where the projection and/or deformable material disposed adjacent to the inner conductor lumen 166 has been deformed and/or collapsed at 180 to electrically and optionally mechanically connect the conductor 120 with the electrode 150. This process is done internal to the electrode 150 without disruption to the outer surface 154 of the electrode 150, for example, by internally staking the conductor 120. The deformation and/or collapsing of at least a part of the lumen 166 allows for at least a portion of the lumen 166 to be collapsed from an uncollapsed position, relative to the conductor 120.

Figure 8:
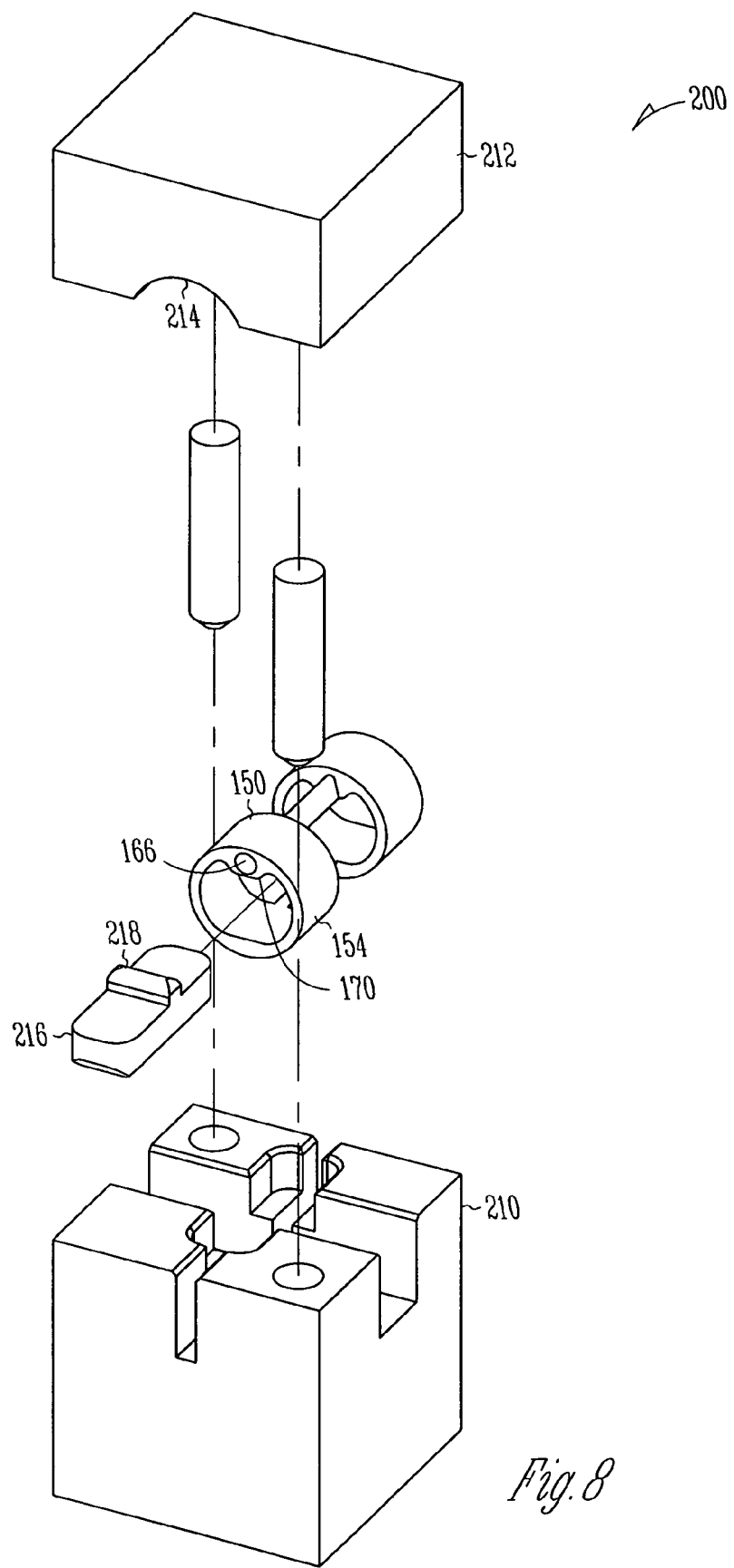
FIG. 8 is an exploded perspective view of a fixture constructed in accordance with at least one embodiment.
Figure 9:
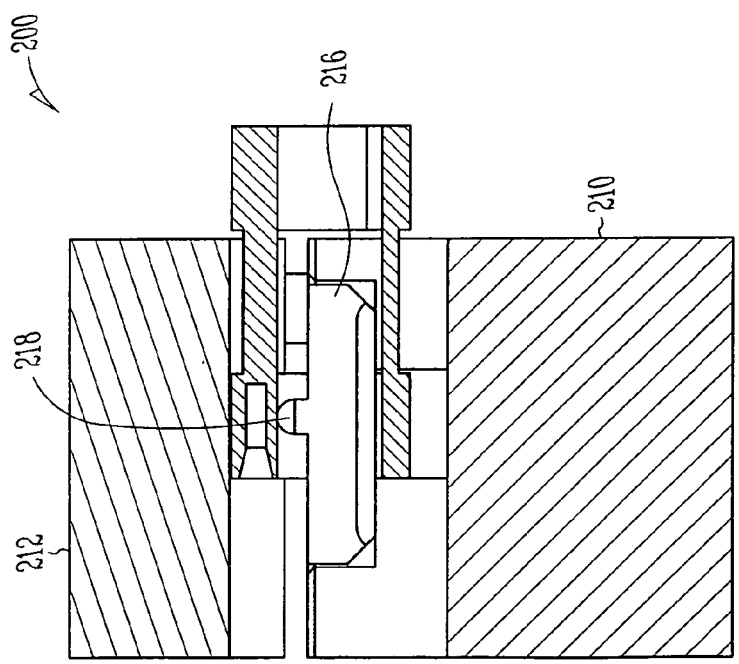
FIG. 9 is a side cross-sectional view of the fixture of FIG. 8.
Figure 10:
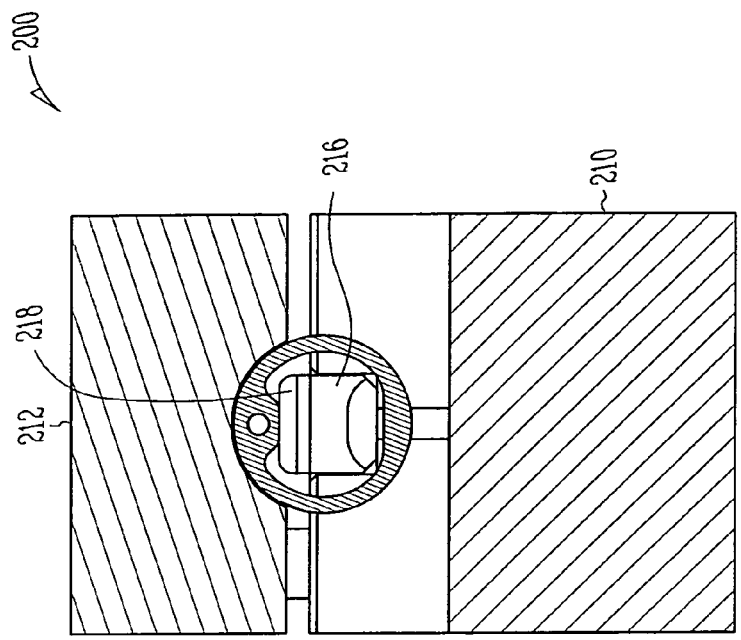
FIG. 10 is a front cross-sectional view of the fixture of FIG. 8.

FIGS. 8-10 illustrate one example of a fixture to connect the conductor with the electrode, for example by deforming the deformable material of the electrode. The fixture 200 includes a base portion 210 and a secondary portion 212 that at least partially encapsulate the electrode 150. The base portion 210 and second portion 212 include features 214 that provide support to the outer surface 154 of the electrode 150 during the deformation process without damaging the outer surface 154 of the electrode 150. The fixture 200 further includes a tool portion 216 that contacts an inner portion of the electrode 150 at 218, providing mechanical force to the inner surface of the electrode 150. The tool portion 216 at 218 can include a number of different structures. For example, the structure at 218 can include, but is not limited to, a rounded outer structure, a pointed structure, etc.

During use of the fixture, the tool portion is moved within a major lumen of the electrode, and aligned with the location of the conductor lumen. The electrode, in one option, is forced on to the tool, allowing for attachment of the conductor.

In another option, the electrode 150 moves toward the tool portion 216 to deform the inner surface of the electrode 150 at 218 of the tool portion 216. It should be noted by deforming the inner surface of the electrode, the outer surface of the electrode can remain pristine. The second portion 212 at 214, for example, moves the electrode 150, and allows for the tool portion 216 to deform the inner surface of the electrode 150. Alternatively, it should be noted that the tool portion 216 can move along the longitudinal axis of the electrode, and move toward the outer surface of electrode, and deforming and/or collapsing the inner surface, for example, a projection within the inner surface. The relative movement between the tool portion 216 and the electrode 150 causes at least a portion of the inner lumen 166 to collapse and/or be deformed. For example, the material is staked to the conductor disposed within the lumen 166. As the material is deformed, optionally, material from the projection or material surrounding the inner lumen 166 flows into one or more recesses 170 of the electrode 150.

During use of the device, the lead having the connector assembly, including the various options discussed above, is introduced within the vasculature of a patient. The energy source, such as the pulse generator and sensor, is implanted subcutaneously within the patient. The connector assembly is electrically coupled with the energy source. For example, the connector assembly is inserted into a socket of the energy source, and the in-line connector assembly, including the connector electrodes 150, 152 form an electrical connection within the energy source.

Advantageously, the connector assembly including the terminal assemblies discussed above, improves reliability for multipolar interconnector assemblies. The terminal connector or other types of electrodes, such as tissue electrodes, can be effectively coupled with the internal conductor without damage to the exterior surface of the terminal connector.

It is to be understood that the above description is intended to be illustrative, and not restrictive. Although the use of the implantable device has been described for use as a lead in, for example, a cardiac stimulation system, the implantable device could as well be applied to other types of body stimulating systems. Many other embodiments will be apparent to those of skill in the art upon reviewing the above description. The scope should, therefore, be determined with reference to the appended claims, along with the full scope of equivalents to which such claims are entitled.

What is claimed is:

1. A lead assembly comprising:
    a lead body extending from a proximal end to a distal end and having an intermediate portion therebetween;
    at least one conductor extending within the lead body;
    a first terminal electrode disposed along the lead body, the first terminal electrode defined in part by an annular-shaped outer contact surface;
    a second terminal electrode disposed along the lead body spaced apart from the first terminal electrode; and
    an electrode interconnect extending between the first terminal electrode and the second terminal electrode and electrically connecting the first terminal electrode to the second terminal electrode;
    the first terminal electrode having a first major inner lumen defined by a first inner surface, the first major inner lumen having a non circular cross-section;
    the first terminal electrode having at least a second inner lumen disposed between the first major lumen and the outer surface, the second inner lumen having a circular cross-section;
    the at least one conductor disposed within the second inner lumen; and
    at least a portion of the first terminal electrode deformed over the at least one conductor.

2. The lead assembly as recited in claim 1, wherein the second inner lumen is defined by a surface, and the surface is a textured surface.

3. The lead assembly as recited in claim 1, further comprising a projection disposed adjacent the second inner lumen.

4. The lead assembly as recited in claim 3, wherein the projection has a collapsed position closing at least a portion of the second inner lumen over at least a portion of the at least one conductor.

5. A lead assembly comprising:
    a lead body extending from a proximal end to a distal end and having an intermediate portion therebetween;
    at least one conductor extending within the lead body;
    a first terminal electrode disposed at or near the proximal end of the lead body, the first terminal electrode defined in part by an annular-shaped outer contact surface;
    a second terminal electrode disposed at or near the proximal end of the lead body, the second terminal electrode spaced apart from the first terminal electrode; and
    an electrode interconnect extending between the first terminal electrode and the second terminal electrode, the electrode interconnect mechanically connecting the first terminal electrode to the second terminal electrode;
    the first terminal electrode having a first major inner lumen defined by a first inner surface, the first major inner lumen having a non-circular cross-section;
    the first terminal electrode having at least a second inner lumen disposed between the first major lumen and the outer surface, the second inner lumen has a first uncollapsed position and a second collapsed position;
    at least one conductor disposed within the second inner lumen; and
    at least one projection disposed adjacent the second position, the projection having a collapsed position closing at least a portion of the second inner lumen over at least a portion of the at least one conductor.

6. The lead assembly as recited in claim 5, further comprising a projection disposed adjacent the second inner lumen.

7. The lead assembly as recited in claim 5, wherein the second inner lumen is defined by a surface, and the surface is a textured surface.

8. The lead assembly as recited in claim 5, wherein the second inner lumen is circular in the first uncollapsed position.

9. A lead assembly comprising:
    a lead body extending from a proximal end to a distal end and having an intermediate portion therebetween;
    at least one conductor extending within the lead body;
    a first terminal electrode disposed at or near the proximal end of the lead body, the first terminal electrode defined in part by an annular-shaped outer contact surface;
    a second terminal electrode disposed at or near the proximal end of the lead body, the second terminal electrode spaced apart from the first terminal electrode; and
    an electrode interconnect extending between the first terminal electrode and the second terminal electrode, the electrode interconnect mechanically connecting the first terminal electrode to the second terminal electrode;
    the first terminal electrode having a first major inner lumen defined by a first inner surface, the first major inner lumen having a non-circular cross-section;
    the first terminal electrode having at least a second inner lumen disposed between the first major lumen and the outer surface, the second inner lumen has a first uncollapsed position and a second collapsed position; and at least one conductor disposed within the second inner lumen;

wherein at least a portion of the first terminal electrode is deformed over the at least one conductor.

10. The lead assembly as recited in claim 9, wherein the second inner lumen is defined by a surface, and the surface is a textured surface.

11. The lead assembly as recited in claim 9, wherein the second inner lumen is circular in the first uncollapsed position.

* * * * *